US006416459B1

(12) United States Patent
Haindl

(10) Patent No.: US 6,416,459 B1
(45) Date of Patent: Jul. 9, 2002

(54) BAG FOR AT LEAST PARTIALLY ENVELOPING A HEART

(75) Inventor: Hans Haindl, Wennigsen (DE)

(73) Assignee: Acorn Cardiovascular Inc., St. Paul, MN (US)

( * ) Notice: Subject to any disclaimer, the term of this patent is extended or adjusted under 35 U.S.C. 154(b) by 0 days.

(21) Appl. No.: 09/453,722

(22) Filed: Dec. 3, 1999

Related U.S. Application Data

(63) Continuation of application No. PCT/EP98/03619, filed on Jun. 16, 1998.

(30) Foreign Application Priority Data

Jun. 21, 1997 (DE) .......................... 197 26 389

(51) Int. Cl.⁷ .............................................. A61F 13/00
(52) U.S. Cl. ..................................................... 600/37
(58) Field of Search ................................ 600/37; 623/3

(56) References Cited

U.S. PATENT DOCUMENTS

| | | | |
|---|---|---|---|
| 3,983,863 A | 10/1976 | Janke et al. | |
| 4,048,990 A | 9/1977 | Goetz | |
| 4,428,375 A | 1/1984 | Ellman | |
| 4,630,597 A | 12/1986 | Kantrowitz et al. | |
| 4,690,134 A | 9/1987 | Snyders | |

FOREIGN PATENT DOCUMENTS

| | | |
|---|---|---|
| DE | 295 17 393 | 1/1997 |
| EP | 0 280 564 A2 | 8/1988 |
| FR | 2 737 106 | 1/1997 |
| JP | 60-203250 A2 | 10/1985 |
| JP | 01-145066 A | 6/1989 |
| SU | 1009457 A | 4/1983 |
| WO | WO 96/16601 | 6/1996 |
| WO | WO 98/29041 | 7/1998 |
| WO | WO 98/58598 | 12/1998 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |

OTHER PUBLICATIONS

International Preliminary Examination Report (8 pages) dated Sep. 22, 1999 (English) for PCT/EP98/03619, filed Jun. 16, 1998.
PCT Schrifticher Bescheid dated Mar. 26, 1999 (6 pgs.).
Internationaler Recherchenbericht dated Oct. 27, 1998 (3 pgs.).
"Supplement to Circulation", *Abstracts from the 68th Scientific Sessions*, vol. 92, No. 8, 2 pages (Oct. 15, 1995).
Capomolla, S. et al., "Dobutamine and nitroprusside infusion in patients with severe congestive heart failure: Hemodynamic improvement by discordant effects on mitral regurgitation, left atrial function, and ventricular function", *American Heart Journal*, pp. 1089–1098 (Dec. 1997).
Capouya, E. et al., "Girdling Effect of Nonsimulated Cardiomyoplasty on Left Ventricular Function", *Ann Thorac. Surg.*, vol. 56, pp. 867–871 (1993).
Cohn, J., "The Management of Chronic Heart Failure", *The New England Journal of Medicine*, vol. 335, No. 7, pp. 490–498 (Aug. 15, 1996).

(List continued on next page.)

Primary Examiner—John P. Lacyk
(74) Attorney, Agent, or Firm—Merchant & Gould P.C.

(57) ABSTRACT

A pouch to at least partly enclose a heart (1), the wall of the pouch (2) being elastic. The purpose of the pouch is to enclose at least part of a heart (1) and to oppose excessive dilation of the heart (1) that might be due to inflammatory disease of the heart muscle, for instance a viral infection or an autoimmune process. In many cases the use of such a pouch (2) may circumvent the need for a heart transplant.

13 Claims, 2 Drawing Sheets

U.S. PATENT DOCUMENTS

| | | |
|---|---|---|
| 4,821,723 A | 4/1989 | Baker, Jr. et al. |
| 4,878,890 A | 11/1989 | Bilweis |
| 4,936,857 A | 6/1990 | Kulik |
| 4,957,477 A | 9/1990 | Lundbäck |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,647,380 A | 7/1997 | Campbell et al. |
| 5,702,343 A | 12/1997 | Alferness |
| 5,713,954 A | 2/1998 | Rosenberg et al. |
| 5,800,528 A | 9/1998 | Lederman et al. |
| 5,961,440 A | 10/1999 | Schweich, Jr. et al. |
| 5,990,378 A | 11/1999 | Ellis |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |

OTHER PUBLICATIONS

Coletta, C. et al., Prognostic value of left ventricular volume response during dobutamine stress echocardiography:, *European Heart Journal*, vol. 18, pp. 1599–1605 (Oct. 1997).

Gusap, F., "Una prótesis contentiva para el tratamiento de la miocardiopatia dilatada", *Revista Española de Cardiologia*, vol. 51, No. 7, pp. 521–528 (Jul. 1998).

Kass, D. et al., "Reverse Remodeling From Cardiomyoplasty in Human Heart Failure External Constraint Versus Active Assist", *Circulation*, vol. 91, No. 9, pp. 2314–2318 (May 1, 1995).

Levin, H. et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh, J. et al., "The Effects of Prosthetic Cardiac Binding and Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, D., "Warp Knitting Technology", *Columbine Press*, p. 111 (1965).

Vaynblat, M. et al., "Cardiac Binding in Experimental Heart Failure", *Ann. Thorac. Surg.*, vol. 64, 11 pages, (1997).

BAG FOR AT LEAST PARTIALLY ENVELOPING A HEART

CROSS REFERENCE TO RELATED APPLICATIONS

This application is a continuation of application PCT/EP98/03619, filed Jun. 16, 1998, which application claims the priority of German application no. 197 26 389.5, filed Jun. 21, 1997, and each of which is incorporated herein by reference.

FIELD OF THE INVENTION

The invention relates to a bag, hereafter called pouch, with which to at least partly enclose a heart.

BACKGROUND OF THE INVENTION

Infectious disease of the heart muscle both by viral infection and by autoimmune processes may lead to enlarged heart volume. If such an enlargement exceeds a critical value, the result will be progressive heart dilation which can be explained by Laplace's law.

As the volume subtended by the left heart chamber increases, the stresses in the walls of this cavity will increase. Consequently the muscle fibrils are overloaded and their ideal range of elongation is exceeded. When this excessive elongation takes place, there is, as a rule, a residual volume in the heart. Then the muscle fibrils must operate against a primarily high wall strain, and are further extended thereby. A vicious cycle arises, leading to increasing distension of the heart and consequent heart insufficiency.

It is basically feasible to treat such a development in its early stages by medicinally lowering the initial load by ACE inhibitors, however such treatment is not always successful. Moreover, on account of initially slight clinical effects, the status will be noticed many times only when a critical point already has been passed. In that case only a heart transplant can be resorted to.

The German patent document U1 295 17 393 discloses a pouch defined in the preamble of claim 1; this pouch however is inelastic and serves to prevent myocardial dilation by the end-diastolic pressure. While this known pouch does prevent cardiac wall distention, it delivers this effect impulsively once the heart volume equals the volume enclosed by the pouch. This impulsive effect adversely affects the heart. Moreover pleats may form in the pouch when the heart volume is less than that subtended by the size of the pouch.

OBJECTS AND SUMMARY OF THE INVENTION

The objective of the invention is to create a pouch with which to at least partly enclose a heart and opposing heart distention without thereby degrading heart function.

The problem basic to the invention is resolved by the disclosure of the characterizing part of claim 1.

The basic concept of the invention is to absorb in part the strains in the wall of the hollow body foremost constituted by the left heart chamber and to relieve thereby the myofibrils. This general effect alone already may prevent enlarging the heart volume beyond a critical value. Accordingly the pouch of the invention offers a support role.

The elasticity function of the invention may be implemented in a number of ways. A very simple implementation calls for the pouch always exerting the same force on the heart regardless of the pouch's elongation, as a result of which the heart, regardless of its volume, shall always be relieved at substantially the same strain. In another appropriate embodiment of the invention, the pouch wall is elastic, whereby the stress it exerts and hence the relief of the heart increases with volume. The characteristics of elongation may be altered depending on the desired relief. Appropriately for instance the pouch wall elasticity decreases with increasing stretching in order to account for the specific strain in the heart wall. Advantageously too, said stretching shall be bounded by a limit value at which the heart no longer can enlarge. Contrary to the known pouch, this limit value cannot be reached impulsively, but because of the elasticity of the pouch of the invention, can be reached only gradually, as a result of which impulsive pouch actions are precluded. The pouch limit value appropriately shall be at a pouch volume corresponding to the heart volume at maximum diastolic filling. On the whole, therefore, the kind of elasticity and the shape of the stretching curve of the pouch allows determining and adapting the myofibril relief implemented by this pouch.

To mount the pouch in place, it can be thorascopically opened and then be drawn over the heart muscle. This motion illustratively proceeds to the anulus fibrosus, that is, the valve plane, where the pouch shall be fixed in place.

In a further embodiment of the invention, the volume of the pouch in its unstretched state is less than the volume of the heart in the stage of minimum filling. As a result, the pouch shall reliably rest against the heart in all stretching phases.

If, as in one embodiment of the invention, the pouch wall is elastic and the stretching is bounded by a limit value, then advantageously the pouch shall be made of an elastic and of an inelastic material. In this case the elastic material determines the stretching function, whereas the inelastic material determines the stretching limit value. Appropriately in practice, the elastic material is made of a threaded sheet or fabric or knit into which are integrated threads made of a substantially inelastic material. The substantially spatially inelastic threads appropriately are longitudinally displaceable in the sheet or fabric or knit.

In this embodiment it is especially advantageous that the substantially inelastic threads be guided segment-wise out of the pouch and in this manner are adapted at maximum diastolic filling by being segment-wise knotted in length and volume to the shape and/or volume of the pouch. In this process the substantially inelastic threads run appropriately from the edge of the pouch aperture to a substantially opposite tip of the pouch. The threads then can be guided out of the pouch in the zone of its tip.

As regards the embodiment wherein the pouch dilation is subject to a limit value, the pouch appropriately consists of a fabric or knit made of inelastic threads while however allowing bending and being crimped transversely to their longitudinal direction. This kind of shaping allows determining the stretching function and the limit value.

Appropriately the pouch wall is a thermoplastic allowing simple shaping of the pouch and adapting it to the shape of the heart, or it may be made of a biological material, denatured bovine pericardium being especially suitable.

To implement permeability to gases, in particular oxygen, and to liquids, the wall of the pouch of the invention appropriately shall be a netting. Such netting appropriately may be made of an open-pore foam, for instance silicone foam. Such a foam assures highly uniform and gentle application of pressure to the heart muscle. Moreover such a foam is able to absorb a lubricant, for instance a serous liquid, thus providing good slippage between pouch and pericardium. Appropriately the lubricant is biological and genetically engineered, hyaluronic acid being especially suitable. By introducing a lubricant beforehand into the foam, good slipping properties are provided from the beginning and as a result primary, self-reinforcing irritation of the pericardium shall be avoided.

If the wall of the pouch of the invention is a netting, then such may be formed as a perforated sheet. Such a sheet is able to transmit the pouch pressure through a large surface to the heart.

The wall of the pouch of the invention also may be a fabric or a knit. In this manner the pouch's stretching behavior can be matched to any particulars within wide limits.

Regardless of the pouch wall netting being constituted by a sheet, fabric or knit, appropriately an additional coating of open-pore foam shall be provided to assure uniform force transmission and also holding any lubricants.

If the elasticity of the pouch wall decreases as stretching increases, or if there is a limit value on stretching, then a special embodiment of the invention provides that the pouch be composed of two kinds of plastic threads or fibers, one kind of higher, and preferably much higher shaping temperature than the other, one kind being elastic and the other kind relatively less, preferably much less elastic than the other. By using such differing fibers, it is possible to thermoplastically shape the pouch at a temperature at which the less elastic or inelastic material remains permanently shaped at a given shaping temperature, though not the more elastic material. The less elastic or inelastic material in this manner determines the maximum pouch stretching whereas the elastic material, which shall return to its initial shape, applies constricting forces on the heart, below the shape determined by the less or inelastic material.

In another embodiment of the invention, the plastic used in manufacturing the pouch is thermoplastic. This feature offers the advantage that not only can the pouch be prefinished in simple manner into a given shape, but also that the pouch can be shaped during surgery, or its shape may be altered during surgery, in order to adapt the dimensions so found to the parts of the heart to be enclosed.

In a further embodiment of the invention the foam is made of silicone.

The objective of the invention furthermore is to propose a method for manufacturing a pouch as defined in claim 1. This problem is resolved by making a mold in the shape of the heart part to be enclosed and in that a gas- and/or liquid-permeable sheet or a netting of knit consisting of a thermoplastic is pulled over the mold while heated.

The structure of the mold appropriately is entailed or determined by imaging the shape of the heart to be enclosed and in is that the mold is produced from this image. The image can be produced in arbitrary manner, for instance by x-rays or computer tomography.

BRIEF DESCRIPTION OF THE DRAWINGS

The invention is elucidated further in relation to the drawings.

DETAILED DESCRIPTION OF THE INVENTION

Figure 1:
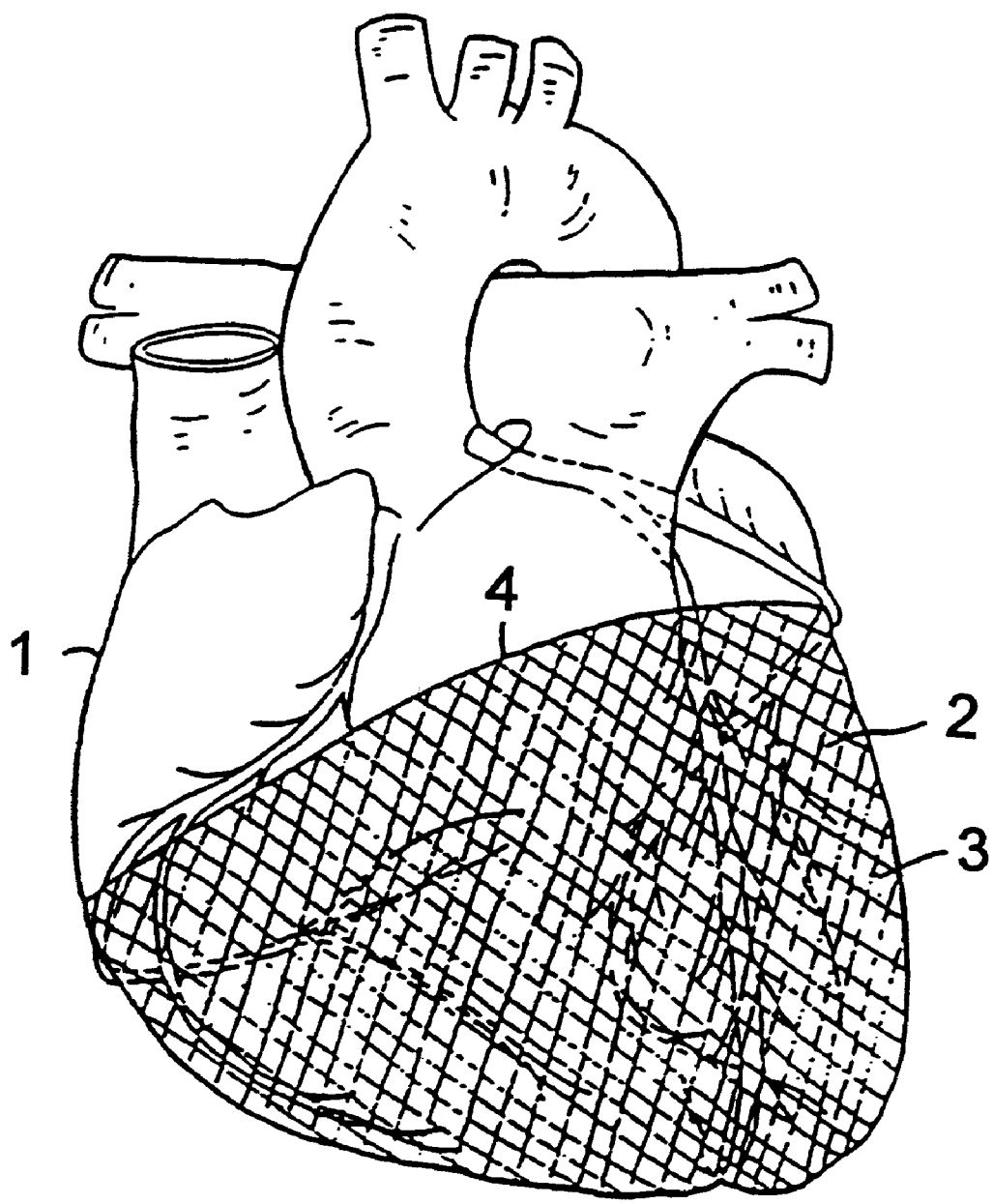
FIG. 1 shows a first embodiment of the invention.

The drawing schematically shows a heart 1 partly enclosed by a pouch 2 of which the wall consists of a netting 3. The pouch 2 reaches as far as into the zone of the anulus fibrosus, that is as far as the valve plane, where it is affixed (omitted from the drawing) to the heart muscle along a selvage 4. The netting 3 consists of elastic threads. In the unstretched state, the volume of the pouch 2 is less than the volume of the heart 1 in the stage of minimum filling. As a result, the netting shall rest against the heart 1 in all stretching stages.

Figure 2:
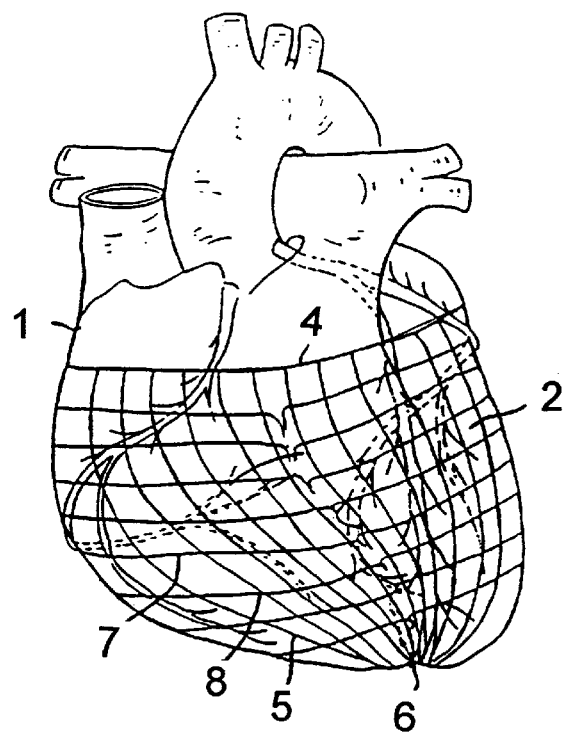
FIG. 2 is a second embodiment of the invention.

FIG. 2 shows a second embodiment of the invention which is a variant of that of FIG. 1. Identical or corresponding components are denoted by identical references. The difference is that threads 5 converge from the selvage 4 into a central point 6, whereas threads 7 run substantially circumferentially. Where they cross at points 8, the threads 5 and 7 are connected to each other, either by being fused, bonded or by dipping the entire pouch 2 into a body of material, for instance foam which shall subsequently solidify.

Figure 3:
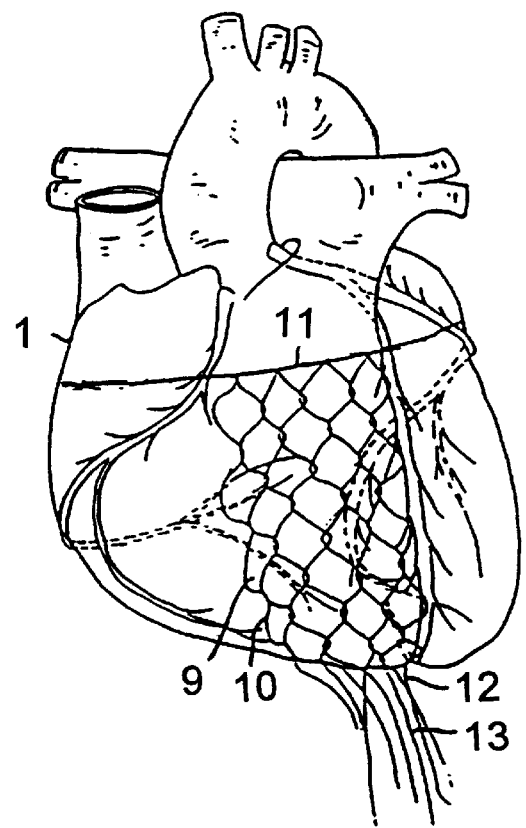
FIG. 3 is a third embodiment of the invention.

FIG. 3 shows an embodiment of a pouch 9 consisting of a knit of threads 10 running from a selvage 11 to a central point 12 where they are bundled away at their ends 13 which, following application of the pouch 9, then can be tensioned or be knotted to one another in order to match thereby the pouch 9 to the shape and volume of the heart 1.

What is claimed is:

1. A pouch adapted to at least partly enclose a heart, the pouch comprising elastic and inelastic material, wherein the elastic material determines a stretching function of the pouch and the inelastic material determines a stretching limit value.

2. The pouch according to claim 1, wherein the elastic material comprises threads into which are incorporated substantially inelastic threads.

3. The pouch according to claim 2, wherein the substantially inelastic threads are incorporated into the elastic material in a longitudinally displaceable manner.

4. The pouch according to claim 1, wherein the inelastic threads comprise one or more crimps, one or more pleats, or accordion geometry that help determine the stretching limit value.

5. The pouch according to claim 2, wherein the inelastic threads have a longitudinal direction, and the threads are crimped transversely to their longitudinal direction.

6. The pouch according to claim 5, wherein the crimps are thermally set.

7. The pouch according to claim 5, wherein the threads are crimped in a wavy or zig-zag manner.

8. The pouch according to claim 3, wherein the pouch has a shape and volume, the heart has a shape and volume at maximum diastolic filling, and the substantially inelastic threads are adjustable in length such that at least one of the shape or volume of the pouch is adapted to correspond to at least one of the shape or volume of the heart at maximum diastolic filling.

9. The pouch according to claim 1, wherein the elastic material comprises a sheet, fabric or a knit.

10. A pouch adapted to at least partly enclose a heart, the pouch comprising:

elastic material comprising threads with substantially non-elastic threads incorporated therein, the pouch defining an aperture edge and a substantially opposite pouch tip, wherein the substantially inelastic threads run from the aperture edge of the pouch to the substantially opposite pouch tip.

11. The pouch according to claim 10, wherein the elastic material comprises a sheet, fabric or a knit.

12. A pouch adapted to at least partly enclose a heart, wherein the pouch comprises an elastic wall comprising two kinds of thermoplastic threads or fibers, one kind of which is of a higher shaping temperature than the other kind, the one kind being elastic and the other kind being relatively less elastic.

13. The pouch according to claim 12, wherein the plastic is thermoplastic.

* * * * *